(12) United States Patent
Dong et al.

(10) Patent No.: US 9,938,310 B2
(45) Date of Patent: Apr. 10, 2018

(54) 1,1'-BIS(PHOSPHINO)FERROCENE LIGANDS FOR ALKOXYCARBONYLATION

(71) Applicant: EVONIK DEGUSSA GMBH, Essen (DE)

(72) Inventors: Kaiwu Dong, Bo Zhou (CN); Helfried Neumann, Rostock (DE); Ralf Jackstell, Cuxhaven Altenwalde (DE); Matthias Beller, Ostseebad Nienhagen (DE); Dirk Fridag, Haltern am See (DE); Dieter Hess, Marl (DE); Katrin Marie Dyballa, Recklinghausen (DE); Frank Geilen, Haltern am See (DE); Robert Franke, Marl (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/649,759

(22) Filed: Jul. 14, 2017

(65) Prior Publication Data

US 2018/0022772 A1    Jan. 25, 2018

(30) Foreign Application Priority Data

Jul. 19, 2016 (EP) ..................... 16180055

(51) Int. Cl.
| | |
|---|---|
| *C07F 15/02* | (2006.01) |
| *C07F 9/58* | (2006.01) |
| *B01J 31/12* | (2006.01) |
| *C07F 17/02* | (2006.01) |
| *C07C 67/38* | (2006.01) |
| *C07C 213/02* | (2006.01) |

(52) U.S. Cl.
CPC ............. *C07F 17/02* (2013.01); *C07C 67/38* (2013.01); *C07C 213/02* (2013.01); *C07C 2527/185* (2013.01)

(58) Field of Classification Search
CPC ............. C07F 15/02; C07F 9/58; B01J 31/12
USPC ................. 546/2, 21; 502/152, 326
See application file for complete search history.

(56) References Cited

U.S. PATENT DOCUMENTS

| | | |
|---|---|---|
| 2017/0022137 A1 | 1/2017 | Dong et al. |
| 2017/0022138 A1 | 1/2017 | Dong et al. |
| 2017/0022139 A1 | 1/2017 | Dong et al. |
| 2017/0022234 A1 | 1/2017 | Jennerjahn et al. |
| 2017/0022235 A1 | 1/2017 | Dong et al. |
| 2017/0022236 A1 | 1/2017 | Dong et al. |

FOREIGN PATENT DOCUMENTS

| | | |
|---|---|---|
| EP | 0662467 A1 | 7/1995 |
| JP | 2000-256384 A | 9/2000 |

OTHER PUBLICATIONS

U.S. Appl. No. 15/649,743, Dong, et al., filed Jul. 14, 2017.
U.S. Appl. No. 15/649,770, Dong, et al., filed Jul. 14, 2017.
U.S. Appl. No. 15/649,781, Dong, et al., filed Jul. 14, 2017.
U.S. Appl. No. 15/651,042, Fang, et al., filed Jul. 17, 2017.
U.S. Appl. No. 15/651,105, Dong, et al., filed Jul. 17, 2017
U.S. Appl. No. 15/651,169, Dong, et al., filed Jul. 17, 2017.
U.S. Appl. No. 15/651,062, Dong, et al., filed Jul. 17, 2017.
European Search Report dated Sep. 14, 2016 for EP 16180055.2 (9 pages).
Malenza, F. et al. Ferrrocenyl diphosphines containing stereogenic phosphorus atoms: Synthesis and application in the rhodium-catalyzed asymmetric hydrogenation. Organometallics, vol. 18, 1999, pp. 1041-1049.
Tsuruta, H. et al. A new P-chiral bisphosphine, 1,1'-bis[(t-butyl)methyl-phosphino]ferrocene, as an effective ligand in catalytic asymmetric hydrosilylation of simple ketones. Tetrahedron Asymmetry, vol. 10, Nr. 5, 1999, pp. 877-882.
Nettekoven, U. et al. Phosphorus-Chiral Analogues of 1,1'-Bis(diphenylphosphino)ferrocene: X Asymmetric Synthesis and Application in Highly Enantioselective Rhodium-Catalyzed Hydrogenation Reactions. Journal of Organic Chemistry, vol. 64, 1999, pp. 3996-4004.
Anderson, B. et al. Substrate and Catalyst Screening in Platinum-Catalyzed Asymmetric Alkylation of Bis(secondary) Phosphines. Synthesis of an Enantiomerically Pure $C_2$—Symmetric Diphosphine. Organometallics, vol. 27, Nr. 19, 2008, pp. 4992-5001.

(Continued)

*Primary Examiner* — Charanjit Aulakh
(74) *Attorney, Agent, or Firm* — Smith, Gambrell and Russell, LLP

(57) ABSTRACT

Diastereomer mixture comprising diastereomers of the formulae (I.1) and (I.2)

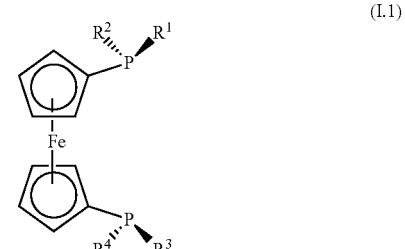

(I.1)

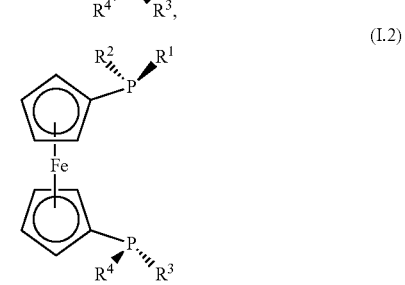

(I.2)

where
$R^2$, $R^4$ are each independently selected from —$(C_1\text{-}C_{12})$-alkyl, —$(C_3\text{-}C_{12})$-cycloalkyl, —$(C_3\text{-}C_{12})$-heterocycloalkyl, —$(C_6\text{-}C_{20})$-aryl;
the $R^1$, $R^3$ radicals are each a —$(C_3\text{-}C_{20})$-heteroaryl radical.
The invention further relates to Pd complex mixtures comprising the diastereomers according to the invention, and to the use thereof in an alkoxycarbonylation process.

20 Claims, No Drawings

(56) References Cited

OTHER PUBLICATIONS

Nettekoven, U. et al. Phosphorus-chiral diphosphines as ligands in a hydroformylation. An investigation on the influence of electronic effects in catalysis. Organometallics, vol. 19, Nr. 22, 2000, pp. 4596-4607.
Bianchini, C. et al. Methoxycarbonylation of ethene by palladium(II) complexes with 1,1'-bis(diphenylphosphino)ferrocene (dppf) and 1,1'-bis(diphenylphosphino) octamethylferrocene (dppomf) Organometallics, vol. 22, Nr. 12, 2003, pp. 2409-2421.
Khokarale, S. et al. Zwitterion enhanced performance in palladium-phosphine catalyzed ethylene methoxycarbonylation. Catalysis Communications, 2014, vol. 44, pp. 73-75.
Clegg, W. et al. Highly active and selective catalysts for the production of propanoate via the methoxycarbonylation of ethane. Chem. Commun. 1999, pp. 1877-1878.
Armarego, W. et al. Purification of Laboratory Chemicals, Butterworth Heinemann (Elsevier), 6th edition, Oxford 2009 (index and chapter abstracts provided).
Harris, R. et al. NMR Nomenclature, Nuclear Spin Properties and Conventions for Chemical Shifts, Pure Appl. Chem., 2001, No. 73, pp. 1795-1818.
Harris, R. et al. Further Conventions for NMR Shielding and Chemical Shifts. Pure Appl. Chem., 2008, No. 80, pp. 59-84.
Köppe, R. et al. Quntenchemische und Experimentelle Untersuchungen zur Stabilität und Struktur von $GaAs_5$ und $InAs_5$. Angew. Chem. 2004 No. 116, pp. 2222-2225.
Budzelaar, P. et al. Synthesis and Coordination Chemistry of a New Class of Binucleating Ligands: Pyridyl-Substituted Diphosphines. Organometallics 1990, No. 9, pp. 1222-1227.

1,1'-BIS(PHOSPHINO)FERROCENE LIGANDS FOR ALKOXYCARBONYLATION

The invention relates to a diastereomer mixture of 1,1'-bis(phosphino)ferrocene compounds, to metal complexes of these compounds and to the use thereof for alkoxycarbonylation.

The alkoxycarbonylation of ethylenically unsaturated compounds is a process of increasing significance. An alkoxycarbonylation is understood to mean the reaction of ethylenically unsaturated compounds (olefins) with carbon monoxide and alcohols in the presence of a metal-ligand complex to give the corresponding esters. Typically, the metal used is palladium. The following scheme shows the general reaction equation of an alkoxycarbonylation:

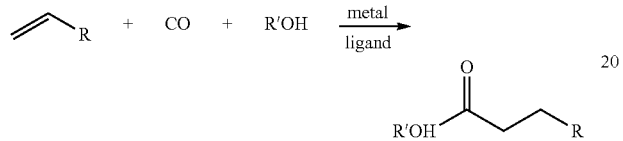

Among the alkoxycarbonylation reactions, particularly the reaction of ethene and methanol to give 3-methylpropionate (ethene methoxycarbonylation) is of significance as an intermediate step for the preparation of methyl methacrylate (S. G. Khokarale, E. J. Garcia-Suárez, J. Xiong, U. V. Mentzel, R. Fehrmann, A. Riisager, Catalysis Communications 2014, 44, 73-75). Ethene methoxycarbonylation is conducted in methanol as solvent under mild conditions with a palladium catalyst modified by phosphine ligands.

Typically, bidentate diphosphine compounds are used here as ligands. A very good catalytic system was developed by Lucite—now Mitsubishi Rayon—and uses a ligand based on 1,2-bis(di-tert-butylphosphinomethyl)benzene (DTBPMB) (W. Clegg, G. R. Eastham, M. R. J. Elsegood, R. P. Tooze, X. L. Wang, K. Whiston, Chem. Commun. 1999, 1877-1878).

Applications of methoxycarbonylation to longer-chain substrates are described, for example, in EP 0 662 467. The patent specification describes a process for preparing dimethyl adipate from methyl 3-pentenoate. The Pd source used is Pd(II) acetate. Examples of suitable bidentate phosphine ligands given include 1,1'-bis(diphenylphosphino)ferrocene, 1-(diphenylphosphino)-1'-(diisopropylphosphino)ferrocene and 1,1'-bis(isopropylphenylphosphino)-ferrocene. However, the ligands achieve only unsatisfactory yields in the methoxycarbonylation of olefins, especially of long-chain olefins such as 2-octene and di-n-butane.

The problem addressed by the present invention is that of providing novel ligands for alkoxycarbonylation, with which good yields of esters can be achieved. More particularly, the ligands according to the invention are to be suitable for the alkoxycarbonylation of long-chain ethylenically unsaturated compounds, for example $C_8$ olefins, and of mixtures of ethylenically unsaturated compounds.

This problem is solved by a diastereomer mixture of 1,1'-bis(phosphino)ferrocene compounds each substituted by at least one heteroaryl radical on the two phosphorus atoms, the mixture comprising two specific diastereomers. It was found here that palladium complexes formed from the diastereomer mixture according to the invention lead to good yields in the alkoxycarbonylation of ethylenically unsaturated compounds, especially of $C_8$ olefins. A separation of the diastereomers and the preparation of diastereomerically pure ligands can thus be dispensed with. Since such a separation is always very inconvenient and costly, the overall process thus also becomes more economically viable. Moreover, a lower level of by-products is obtained, since it is possible in this case to use a mixture of the diastereomers and there is no need to dispose of one of the diastereomers.

The diastereomer mixture according to the invention comprises diastereomers of the formulae (I.1) and (I.2)

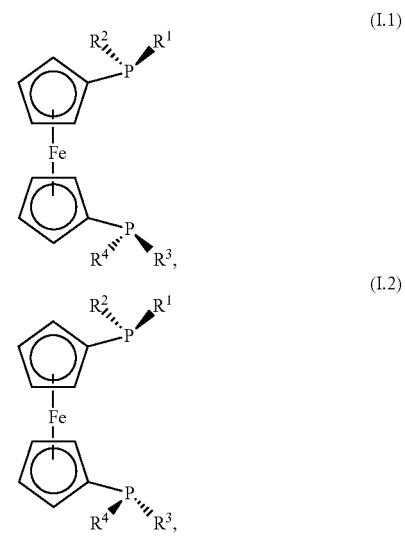

where
$R^2$, $R^4$ are each independently selected from $—(C_1-C_{12})$-alkyl, $—(C_3-C_{12})$-cycloalkyl, $—(C_3-C_{12})$-heterocycloalkyl, $—(C_6-C_{20})$-aryl;
the $R^1$, $R^3$ radicals are each a $—(C_3-C_{20})$-heteroaryl radical;
$R^1$, $R^3$ may each independently be substituted by one or more substituents selected from $—(C_1-C_{12})$-alkyl, $—(C_3-C_{12})$-cycloalkyl, $—(C_3-C_{12})$-heterocycloalkyl, $—O—(C_1-C_{12})$-alkyl, $—O—(C_1-C_{12})$-alkyl-$(C_6-C_{20})$-aryl, $—O—(C_3-C_{12})$-cycloalkyl, $—S—(C_1-C_{12})$-alkyl, $—S—(C_3-C_{12})$-cycloalkyl, $—COO—(C_1-C_{12})$-alkyl, $—COO—(C_3-C_{12})$-cycloalkyl, $—CONH—(C_1-C_{12})$-alkyl, $—CONH—(C_3-C_{12})$-cycloalkyl, $—CO—(C_1-C_{12})$-alkyl, $—CO—(C_3-C_{12})$-cycloalkyl, $—N—[(C_1-C_{12})$-alkyl$]_2$, $—(C_6-C_{20})$-aryl, $—(C_6-C_{20})$-aryl-$(C_1-C_{12})$-alkyl, $—(C_6-C_{20})$-aryl-$O—(C_1-C_{12})$-alkyl, $—(C_3-C_{20})$-heteroaryl, $—(C_3-C_{20})$-heteroaryl-$(C_1-C_{12})$-alkyl, $—(C_3-C_{20})$-heteroaryl-$O—(C_1-C_{12})$-alkyl, $—COOH$, $—OH$, $—SO_3H$, $—NH_2$, halogen; and
$R^2$, $R^4$, if they are $—(C_1-C_{12})$-alkyl, $—(C_3-C_{12})$-cycloalkyl, $—(C_3-C_{12})$-heterocycloalkyl or $—(C_6-C_{20})$-aryl, may each independently be substituted by one or more substituents selected from $—(C_1-C_{12})$-alkyl, $—(C_3-C_{12})$-cycloalkyl, $—(C_3-C_{12})$-heterocycloalkyl, $—O—(C_1-C_{12})$-alkyl, $—O—(C_1-C_{12})$-alkyl-$(C_6-C_{20})$-aryl, $—O—(C_3-C_{12})$-cycloalkyl, $—S—(C_1-C_{12})$-alkyl, $—S—(C_3-C_{12})$-cycloalkyl, $—COO—(C_1-C_{12})$-alkyl, $—COO—(C_3-C_{12})$-cycloalkyl, $—CONH—(C_1-C_{12})$-alkyl, $—CONH—(C_3-C_{12})$-cycloalkyl, $—CO—(C_1-C_{12})$-alkyl, $—CO—(C_3-C_{12})$-cycloalkyl, $—N—[(C_1-C_{12})$-alkyl$]_2$, $—(C_6-C_{20})$-aryl, $—(C_6-C_{20})$-aryl-$(C_1-C_{12})$-alkyl, $—(C_6-C_{20})$-aryl-$O—(C_1-C_{12})$-alkyl, $—(C_3-C_{20})$-heteroaryl, $—(C_3-C_{20})$-heteroaryl-$(C_1-C_{12})$-alkyl, $—(C_3-C_{20})$-heteroaryl-$O—(C_1-C_{12})$-alkyl, $—COOH$, $—OH$, $—SO_3H$, $—NH_2$, halogen.

It has been found that the diastereomer mixture according to the invention leads to an effective catalyst especially if the two diastereomers are present in a particular molar ratio. Thus, the molar ratio of (I.1) to (I1.2) is preferably in the range from 10:90 to 70:30, especially from 20:80 to 60:40, more preferably from 30:70 to 50:50, most preferably from 35:65 to 45:55.

The expression $(C_1$-$C_{12})$-alkyl encompasses straight-chain and branched alkyl groups having 1 to 12 carbon atoms. These are preferably $(C_1$-$C_8)$-alkyl groups, more preferably $(C_1$-$C_6)$-alkyl, most preferably $(C_1$-$C_4)$-alkyl.

Suitable $(C_1$-$C_{12})$-alkyl groups are especially methyl, ethyl, propyl, isopropyl, n-butyl, iso-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression $(C_1$-$C_{12})$-alkyl also apply particularly to the alkyl groups in —O—$(C_1$-$C_{12})$-alkyl, —S—$(C_1$-$C_{12})$-alkyl, —COO—$(C_1$-$C_{12})$-alkyl, —CONH—$(C_1$-$C_{12})$-alkyl, —CO—$(C_1$-$C_{12})$-alkyl and —N—[$(C_1$-$C_{12})$-alkyl]$_2$.

The expression $(C_3$-$C_{12})$-cycloalkyl encompasses mono-, bi- or tricyclic hydrocarbyl groups having 3 to 12 carbon atoms. Preferably, these groups are $(C_5$-$C_{12})$-cycloalkyl.

The $(C_3$-$C_{12})$-cycloalkyl groups have preferably 3 to 8, more preferably 5 or 6, ring atoms, Suitable $(C_3$-$C_{12})$-cycloalkyl groups are especially cyclopropyl, cyclobutyl, cyclopentyl, cyclohexyl, cycloheptyl, cyclooctyl, cyclododecyl, cyclopentadecyl, norbornyl, adamantyl.

The elucidations relating to the expression $(C_3$-$C_{12})$-cycloalkyl also apply particularly to the cycloalkyl groups in —O—$(C_3$-$C_{12})$-cycloalkyl, —S—$(C_3$-$C_{12})$-cycloalkyl, —COO—$(C_3$-$C_{12})$-cycloalkyl, —CONH—$(C_3$-$C_{12})$-cycloalkyl, —CO—$(C_3$-$C_{12})$-cycloalkyl.

The expression $(C_3$-$C_{12})$-heterocycloalkyl encompasses nonaromatic, saturated or partly unsaturated cycloaliphatic groups having 3 to 12 carbon atoms, where one or more of the ring carbon atoms are replaced by heteroatoms. The $(C_3$-$C_{12})$-heterocycloalkyl groups have preferably 3 to 8, more preferably 5 or 6, ring atoms and are optionally substituted by aliphatic side chains. In the heterocycloalkyl groups, as opposed to the cycloalkyl groups, one or more of the ring carbon atoms are replaced by heteroatoms or heteroatom-containing groups. The heteroatoms or the heteroatom-containing groups are preferably selected from O, S, N, N(=O), C(=O), S(=O). A $(C_3$-$C_{12})$-heterocycloalkyl group in the context of this invention is thus also ethylene oxide.

Suitable $(C_3$-$C_{12})$-heterocycloalkyl groups are especially tetrahydrothiophenyl, tetrahydrofuryl, tetrahydropyranyl and dioxanyl.

The expression $(C_6$-$C_{20})$-aryl encompasses mono- or polycyclic aromatic hydrocarbyl radicals having 6 to 20 carbon atoms. These are preferably $(C_6$-$C_{14})$-aryl, more preferably $(C_6$-$C_{10})$-aryl.

Suitable $(C_6$-$C_{20})$-aryl groups are especially phenyl, naphthyl, indenyl, fluorenyl, anthracenyl, phenanthrenyl, naphthacenyl, chrysenyl, pyrenyl, coronenyl. Preferred $(C_6$-$C_{20})$-aryl groups are phenyl, naphthyl and anthracenyl.

The expression $(C_3$-$C_{20})$-heteroaryl encompasses mono- or polycyclic aromatic hydrocarbyl radicals having 3 to 20 carbon atoms, where one or more of the carbon atoms are replaced by heteroatoms. Preferred heteroatoms are N, O and S. The $(C_3$-$C_{20})$-heteroaryl groups have 3 to 20, preferably 6 to 14 and more preferably 6 to 10 ring atoms. Thus, for example, pyridyl in the context of this invention is a $C_6$-heteroaryl radical; furyl is a $C_5$-heteroaryl radical.

Suitable $(C_3$-$C_{20})$-heteroaryl groups are especially furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl.

The expression halogen especially encompasses fluorine, chlorine, bromine and iodine. Particular preference is given to fluorine and chlorine.

In one embodiment, the $R^1$, $R^3$ radicals may each independently be substituted by one or more substituents selected from —$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —S—$(C_1$-$C_{12})$-alkyl, —S—$(C_3$-$C_{12})$-cycloalkyl, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_6$-$C_{20})$-heteroaryl-O—$(C_1$-$C_{12})$-alkyl, —COOH, —OH, —SO$_3$H, —NH$_2$, halogen.

In one embodiment, the $R^1$, $R^3$ radicals may each independently be substituted by one or more substituents selected from —$(C_1$-$C_{12})$-alkyl, —$(C_3$-$C_{12})$-cycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —$(C_6$-$C_{20})$-aryl, —$(C_6$-$C_{20})$-aryl, —$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl.

In one embodiment, the $R^1$, $R^3$ radicals may each independently be substituted by one or more substituents selected from —$(C_1$-$C_{12})$-alkyl, —O—$(C_1$-$C_{12})$-alkyl-$(C_3$-$C_{20})$-aryl, —$(C_3$-$C_{20})$-heteroaryl, —$(C_3$-$C_{20})$-heteroaryl-$(C_1$-$C_{12})$-alyl, —$(C_3$-$C_{20})$-heteroaryl-O—$(C_1$-$C_{12})$-alkyl.

In one embodiment, the $R^1$, $R^3$ radicals may each independently be substituted by one or more substituents selected from —$(C_1$-$C_{12})$-alkyl and —$(C_3$-$C_{20})$-heteroaryl.

In one embodiment, the $R^1$, $R^3$ radicals are unsubstituted.

In one embodiment, the $R^2$, $R^4$ radicals, if they are —$(C_1$-$C_{12})$-alkyl, —$(C_3$-$C_{12})$-cycloalkyl, —$(C_3$-$C_{12})$-heterocyoalkyl or —$(C_6$-$C_{20})$-aryl, may each independently be substituted by one or more substituents selected from —$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —S—$(C_1$-$C_{12})$-alkyl, —S—$(C_3$-$C_{12})$-cycloalkyl, —$(C_6$-$C_{20})$-aryl, —$(C_6$-$C_{20})$-aryl-$(C_1$-$C_{12})$-alkl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroary-O—$(C_1$-$C_{12})$-alkyl, —COOH, —OH, —SO$_3$H, —NH$_2$, halogen.

In one embodiment, the $R^2$, $R^4$ radicals, if they are —$(C_1$-$C_{12})$-alkyl, —$(C_3$-$C_2)$-cycloalkyl, —$(C_3$-$C_{12})$-heterocycloalkyl or —$(C_6$-$C_{20})$-aryl, may each independently be substituted by one or more substituents selected from —$(C_1$-$C_{12})$-alkyl, —$(C_3$-$C_{12})$-cycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl.

In one embodiment, the $R^2$, $R^4$ radicals, if they are —$(C_1$-$C_{12})$-alkyl, —$(C_3$-$C_{12})$-cycloalkyl, —$(C_3$-$C_{12})$-heterocycloalkyl or —$(C_3$-$C_{20})$-aryl, may each independently be substituted by one or more substituents selected from —$(C_1-C_{12})$-alkyl, —O—$(C_1-C_{12})$-alkyl-$(C_6-C_{20})$-aryl, —$(C_3-C_{20})$-heteroaryl, —$(C_3-C_{20})$-heteroaryl-$(C_1-C_{12})$-alkyl, —$(C_3-C_{20})$-heteroary-O—$(C_1-C_{12})$-alkyl.

In one embodiment, the $R^2$, $R^4$ radicals, if they are —$(C_1-C_{12})$-alkyl, —$(C_1-C_{12})$-cycloalkyl, —$(C_3-C_{12})$-heterocycloalkyl or —$(C_6-C_{20})$-aryl, may each independently be substituted by one or more substituents selected from —$(C_1-C_{12})$-alkyl and —$(C_3-C_{20})$-heteroaryl.

In one embodiment, the $R^2$, $R^4$ radicals are unsubstituted if they are —$(C_1-C_{12})$-alkyl, —$(C_3-C_{12})$-cycloalkyl or —$(C_3-C_{12})$-heterocycloalkyl, and may be substituted as described if they are —$(C_6-C_{20})$-aryl.

In one embodiment, the $R^2$, $R^4$ radicals are unsubstituted if they are —$(C_1-C_{12})$-alkyl, —$(C_3-C_{12})$-cycloalkyl, —$(C_3-C_{12})$-heterocycloalkyl or —$(C_6-C_{20})$-aryl.

Preferably, $R^2$, $R^4$ are each independently selected from —$(C_1-C_{12})$-alkyl, —$(C_3-C_{12})$-cycloalkyl, —$(C_6-C_{20})$-aryl, more preferably from —$(C_1-C_{12})$-alkyl, cyclohexyl and phenyl. Most preferably, $R^2$, $R^4$ are each —$(C_1-C_{12})$-alkyl. $R^2$, $R^4$ here may be substituted as described above. However, $R^2$, $R^4$ are preferably unsubstituted.

Preferably $R^1$, $R^3$ are each independently selected from heteroaryl radicals having five to ten ring atoms, preferably five or six ring atoms.

In one embodiment, the $R^1$, $R^3$ radicals are each a heteroaryl radical having five ring atoms.

In one embodiment, the $R^1$, $R^3$ radicals are each independently selected from heteroaryl radicals having six to ten ring atoms.

In one embodiment, the $R^1$, $R^3$ radicals are each a heteroaryl radical having six ring atoms.

In one embodiment, the $R^1$, $R^3$ radicals are selected from furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl, where the heteroaryl radicals mentioned may be substituted as described above.

In one embodiment, the $R^1$, $R^3$ radicals are selected from furyl, thienyl, pyrrolyl, imidazolyl, pyridyl, pyrimidyl, indolyl, where the heteroaryl radicals mentioned may be substituted as described above.

In one embodiment, the $R^1$, $R^3$ radicals are selected from 2-furyl, 2-thienyl, 2-pyrrolyl, 2-imidazolyl, 2-pyridyl, 2-pyrimidyl, 2-indolyl, where the heteroaryl radicals mentioned may be substituted as described above.

In one embodiment, the $R^1$, $R^3$ radicals are selected from 2-furyl, 2-thienyl, N-methyl-2-pyrrolyl, N-phenyl-2-pyrrolyl, N-(2-methoxyphenyl)-2-pyrrolyl, 2-pyrrolyl, N-methyl-2-imidazolyl, 2-imidazolyl, 2-pyridyl, 2-pyrimidyl, N-phenyl-2-indolyl, 2-indolyl, where the heteroaryl radicals mentioned have no further substitution.

Preferably, the $R^1$, $R^3$ radicals are pyridyl, especially 2-pyridyl.

In one embodiment, $R^1$ and $R^3$ are a pyridyl radical, preferably 2-pyridyl, and $R^2$ and $R^4$ are —$(C_1-C_{12})$-alkyl, where $R^1$, $R^2$, $R^3$ and $R^4$ may each be substituted as described above.

In one embodiment, the $R^1$ and $R^3$ radicals are identical to one another. In this embodiment, the $R^2$ and $R^4$ radicals are likewise identical to one another.

In one embodiment, the diastereomers I.1 and I.2 according to the invention are compounds of the formulae (8.1) and (8.2):

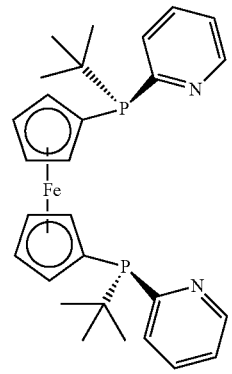

(8.1)

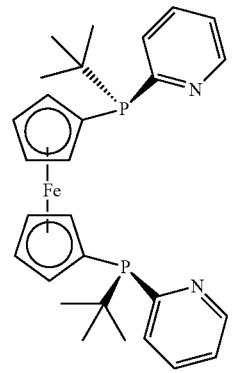

(8.2)

The invention further relates to complex mixtures comprising a first complex comprising Pd and a diastereomer of formula (I.1) according to the invention and a second complex comprising Pd and a diastereomer of formula (I.2) according to the invention. In these complexes, the diastereomers I.1 and I.2 according to the invention serve as bidentate ligands for the metal atom. The complexes serve, for example, as catalysts for alkoxycarbonylation. With the complexes according to the invention, it is possible to achieve high yields in the alkoxycarbonylation of a multitude of different ethylenically unsaturated compounds.

The molar ratio of the first complex to the second complex is preferably in the range from 10:90 to 70:30, especially from 20:80 to 60:40, preferably from 30:70 to 50:50, most preferably from 35:65 to 45:55.

The complexes according to the invention may also comprise further ligands which coordinate to the metal atom. These are, for example, ethylenically unsaturated compounds or anions. Suitable additional ligands are, for example, styrene, acetate anions, maleimides (e.g. N-methylmaleimide), 1,4-naphthoquinone, trifluoroacetate anions or chloride anions.

The invention further relates to the use of a diastereomer mixture according to the invention for catalysis of an alkoxycarbonylation reaction. The diastereomers according to the invention can especially be used as a metal complex mixture according to the invention.

The invention also relates to a process comprising the process steps of:
a) initially charging an ethylenically unsaturated compound;
b) adding a diastereomer mixture according to the invention and a compound comprising Pd,
   or adding a complex mixture according to the invention;
c) adding an alcohol;
d) feeding in CO;

e) heating the reaction mixture, with conversion of the ethylenically unsaturated compound to an ester.

In this process, process steps a), b), c) and d) can be effected in any desired sequence. Typically, however, the addition of CO is effected after the co-reactants have been initially charged in steps a) to c). Steps d) and e) can be effected simultaneously or successively. In addition, CO can also be fed in two or more steps, in such a way that, for example, a portion of the CO is first fed in, then the mixture is heated, and then a further portion of CO is fed in.

The ethylenically unsaturated compounds used as reactant in the process according to the invention contain one or more carbon-carbon double bonds. These compounds are also referred to hereinafter as olefins for simplification. The double bonds may be terminal or internal.

Preference is given to ethylenically unsaturated compounds having 2 to 30 carbon atoms, preferably 2 to 22 carbon atoms, more preferably 2 to 12 carbon atoms.

In one embodiment, the ethylenically unsaturated compound comprises 2 to 30 carbon atoms, preferably 6 to 22 carbon atoms, more preferably 8 to 12 carbon atoms. In an especially preferred embodiment, the ethylenically unsaturated compound comprises 8 carbon atoms.

The ethylenically unsaturated compounds may, in addition to the one or more double bonds, contain further functional groups. Preferably, the ethylenically unsaturated compound comprises one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, hydroxyl, sulphhydryl, amino, ether, thioether, aryl, heteroaryl or silyl groups and/or halogen substituents. At the same time, the ethylenically unsaturated compound preferably comprises a total of 2 to 30 carbon atoms, preferably 2 to 22 carbon atoms, more preferably 2 to 12 carbon atoms.

In one embodiment, the ethylenically unsaturated compound does not comprise any further functional groups apart from carbon-carbon double bonds.

In a particularly preferred embodiment, the ethylenically unsaturated compound is an unfunctionalized alkene having at least one double bond and 2 to 30 carbon atoms, preferably 6 to 22 carbon atoms, further preferably 8 to 12 carbon atoms, and most preferably 8 carbon atoms.

Suitable ethylenically unsaturated compounds are, for example:
ethene;
propene;
C4 olefins such as 1-butene, cis-2-butene, trans-2-butene, mixture of cis- and trans-2-butene, isobutene, 1,3-butadiene; raffinate I to III, crack-C4
C5 olefins such as 1-pentene, 2-pentene, 2-methyl-1-butene, 2-methyl-2-butene, 2-methyl-1,3-butadiene (isoprene), 1,3-pentadiene;
C6 olefins such as tetramethylethylene, 1,3-hexadiene, 1,3-cyclohexadiene;
C7 olefins such as 1-methylcyclohexene, 2,4-heptadiene, norbornadiene;
C8 olefins such as 1-octene, 2-octene, cyclooctene, di-n-butene, diisobutene, 1,5-cyclooctadiene, 1,7-octadiene;
C9 olefins such as tripropene;
C10 olefins such as dicyclopentadiene;
undecenes;
dodecenes;
internal C14 olefins;
internal C15 to C18 olefins;
linear or branched, cyclic, acyclic or partly cyclic, internal C15 to C30 olefins; triisobutene, tri-n-butene;
terpenes such as limonene, geraniol, farnesol, pinene, myrcene, carvone, 3-carene;
polyunsaturated compounds having 18 carbon atoms, such as linoleic acid or linolenic acid;
esters of unsaturated carboxylic acids, such as vinyl esters of acetic or propionic acid, alkyl esters of unsaturated carboxylic acids, methyl or ethyl esters of acrylic acid and methacrylic acid, oleic esters, such as methyl or ethyl oleate, esters of linoleic or linolenic acid;
vinyl compounds such as vinyl acetate, vinylcyclohexene, styrene, alpha-methylstyrene, 2-isopropenylnaphthalene;
2-methyl-2-pentenal, methyl 3-pentenoate, methacrylic anhydride.

In one variant of the process, the ethylenically unsaturated compound is selected from propene, 1-butene, cis- and/or trans-2-butene, or mixtures thereof.

In one variant of the process, the ethylenically unsaturated compound is selected from 1-pentene, cis- and/or trans-2-pentene, 2-methyl-1-butene, 2-methyl-2-butene, 3-methyl-1-butane, or mixtures thereof.

In a preferred embodiment, the ethylenically unsaturated compound is selected from ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, n-octene, 1-octene, 2-octene, or mixtures thereof In one variant, a mixture of ethylenically unsaturated compounds is used. A mixture in the context of this invention refers to a composition comprising at least two different ethylenically unsaturated compounds, where the proportion of each individual ethylenically unsaturated compound is preferably at least 5% by weight, based on the total weight of the mixture.

Preference is given to using a mixture of ethylenically unsaturated compounds each having 2 to 30 carbon atoms, preferably 4 to 22 carbon atoms, more preferably 6 to 12 carbon atoms, most preferably 8 to 10 carbon atoms.

Suitable mixtures of ethylenically unsaturated compounds are those called raffinates I to III. Raffinate I comprises 40% to 50% isobutene, 20% to 30% 1-butene, 10% to 20% cis- and trans-2-butene, up to 1% 1,3-butadiene and 10% to 20% n-butane and isobutane. Raffinate II is a portion of the $C_4$ fraction which arises in naphtha cracking and consists essentially of the isomeric n-butenes, isobutane and n-butane after removal of isobutene from raffinate I. Raffinate III is a portion of the $C_4$ fraction which arises in naphtha cracking and consists essentially of the isomeric n-butenes and n-butane.

A further suitable mixture is di-n-butene, also referred to as dibutene, DNB or DnB. Di-n-butene is an isomer mixture of C8 olefins which arises from the dimerization of mixtures of 1-butene, cis-2-butene and trans-2-butene. In industry, raffinate II or raffinate III streams are generally subjected to a catalytic oligomerization, wherein the butanes present (n/iso) emerge unchanged and the olefins present are converted fully or partly. As well as dimeric di-n-butene, higher oligomers (tributene C12, tetrabutene C16) generally also form, which are removed by distillation after the reaction. These can likewise be used as reactants.

In a preferred variant, a mixture comprising isobutene, 1-butene, cis- and trans-2-butene is used. Preferably, the mixture comprises 1-butene, cis- and trans-2-butene.

The alkoxycarbonylation according to the invention is catalysed by the Pd complexes according to the invention. The Pd complexes may either be added in process step b) as preformed complexes comprising Pd and the diastereomer mixture according to the invention or be formed in situ from a compound comprising Pd and the free diastereomer mixture. In this context, the compound comprising Pd is also referred to as catalyst precursor.

In the case that the catalyst is formed in situ, the diastereomer mixture can be added in excess, such that the unbound ligand is also present in the reaction mixture.

In one variant, the compound comprising Pd is selected from palladium chloride ($PdCl_2$), palladium(II) acetylacetonate [$Pd(acac)_2$], palladium(II) acetate [$Pd(OAc)_2$], dichloro (1,5-cyclooctadiene)palladium(II) [$Pd(cod)_2Cl_2$], bis(dibenzylideneacetone)palladium [$Pd(dba)_2$], bis(acetonitrile) dichloropalladium(II) [$Pd(CH_3CN)_2Cl_2$], palladium (cinnamyl) dichloride [$Pd(cinnamyl)Cl_2$].

Preferably, the compound comprising Pd is $PdCl_2$, $Pd(acac)_2$ or $Pd(OAc)_2$. $PdCl_2$ is particularly suitable.

The alcohol in process step c) may be branched or linear, cyclic, alicyclic, partly cyclic or aliphatic, and is especially a $C_1$- to $C_{30}$-alkanol. It is possible to use monoalcohols or polyalcohols.

The alcohol in process step c) comprises preferably 1 to 30 carbon atoms, more preferably 1 to 22 carbon atoms, especially preferably 1 to 12 carbon atoms. It may be a monoalcohol or a polyalcohol.

The alcohol may, in addition to the one or more hydroxyl groups, contain further functional groups. Preferably, the alcohol may additionally comprise one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, sulphhydryl, amino, ether, thioether, aryl, heteroaryl or silyl groups and/or halogen substituents.

In one embodiment, the alcohol does not comprise any further functional groups except for hydroxyl groups.

The alcohol may contain unsaturated and aromatic groups. However, it is preferably an aliphatic alcohol.

An aliphatic alcohol in the context of this invention refers to an alcohol which does not comprise any aromatic groups, i.e., for example, an alkanol, alkenol or alkynol. Unsaturated nonaromatic alcohols are thus also permitted.

In one embodiment, the alcohol is an alkanol having one or more hydroxyl groups and 1 to 30 carbon atoms, preferably 1 to 22 carbon atoms, more preferably 1 to 12 carbon atoms, most preferably 1 to 6 carbon atoms.

In one variant of the process, the alcohol in process step c) is selected from the group of the monoalcohols.

In one variant of the process, the alcohol in process step c) is selected from: methanol, ethanol, 1-propanol, isopropanol, isobutanol, tert-butanol, 1-butanol, 2-butanol, 1-pentanol, 2-pentanol, 3-pentanol, 1-hexanol, cyclohexanol, phenol, 2-ethylhexanol, isononanol, 2-propylheptanol.

In a preferred variant, the alcohol in process step c) is selected from methanol, ethanol, 1-propanol, 1-butanol, 1-pentanol, 1-hexanol, 2-propanol, tert-butanol, 3-pentanol, cyclohexanol, phenol, and mixtures thereof.

In one variant of the process, the alcohol in process step c) is selected from the group of the polyalcohols.

In one variant of the process, the alcohol in process step c) is selected from: diols, triols, tetraols.

In one variant of the process, the alcohol in process step c) is selected from: cyclohexane-1,2-diol, ethane-1,2-diol, propane-1,3-diol, glycerol, butane-1,2,4-triol, 2-hydroxymethyl-propane-1,3-diol, 1,2,6-trihydroxyhexane, pentaerythritol, 1,1,1-tri(hydroxymethyl)ethane, catechol, resorcinol and hydroxyhydroquinone.

In one variant of the process, the alcohol in process step c) is selected from: sucrose, fructose, mannose, sorbose, galactose and glucose.

In a preferred embodiment of the process, the alcohol in process step c) is selected from methanol, ethanol, 1-propanol, 1-butanol, 1-pentanol, 1-hexanol.

In a particularly preferred variant of the process, the alcohol in process step c) is selected from: methanol, ethanol.

In a particularly preferred variant of the process, the alcohol in process step c) is methanol.

In one variant of the process, the alcohol in process step c) is used in excess.

In one variant of the process, the alcohol in process step c) is used simultaneously as solvent.

In one variant of the process, a further solvent is used, selected from: toluene, xylene, tetrahydrofuran (THF) and methylene chloride ($CH_2Cl_2$).

CO is fed in step d) preferably at a partial CO pressure between 0.1 and 10 MPa (1 to 100 bar), preferably between 1 and 8 MPa (10 to 80 bar), more preferably between 2 and 4 MPa (20 to 40 bar).

The reaction mixture is heated in step e) of the process according to the invention preferably to a temperature between 10° C. and 180° C., preferably between 20 and 160° C., more preferably between 40 and 120° C., in order to convert the ethylenically unsaturated compound to an ester.

The molar ratio of the ethylenically unsaturated compound initially charged in step a) to the alcohol added in step c) is preferably between 1:1 and 1:20, more preferably 1:2 to 1:10, more preferably 1:3 to 1:4.

The mass ratio of Pd to the ethylenically unsaturated compound initially charged in step a) is preferably between 0.001% and 0.5% by weight, preferably between 0.01% and 0.1% by weight, more preferably between 0.01% and 0.05% by weight.

The molar ratio of the diastereomer mixture according to the invention to Pd is preferably between 0.1:1 and 400:1, preferably between 0.5:1 and 400:1, more preferably between 1:1 and 100:1, most preferably between 2:1 and 50:1. Said molar ratio corresponds to the ratio of the total molar amount of both diastereomers 1.1 and 1.2 to the molar amount of Pd.

Preferably, the process is conducted with addition of an acid. In one variant, the process therefore additionally comprises step c'): adding an acid to the reaction mixture. This may preferably be a Brønsted or Lewis acid.

Suitable Brønsted acids preferably have an acid strength of $pK_a \le 5$, preferably an acid strength of $pK_a \le 3$. The reported acid strength $pK_a$ is based on the $pK_a$ determined under standard conditions (25° C., 1.01325 bar). In the case of a polyprotic acid, the acid strength $pK_a$ in the context of this invention relates to the $pK_a$ of the first protolysis step.

Preferably, the acid is not a carboxylic acid.

Suitable Brønsted acids are, for example, perchloric acid, sulphuric acid, phosphoric acid, methylphosphonic acid and sulphonic acids. Preferably, the acid is sulphuric acid or a sulphonic acid. Suitable sulphonic acids are, for example, methanesulphonic acid, trifluoromethanesulphonic acid, tert-butanesulphonic acid, p-toluenesulphonic acid (PTSA), 2-hydroxypropane-2-sulphonic acid, 2,4,6-trimethylbenzenesulphonic acid and dodecylsulphonic acid. Particularly preferred acids are sulphuric acid, methanesulphonic acid, trifluoromethanesulphonic acid and p-toluenesulphonic acid.

A Lewis acid used may, for example, be aluminium triflate.

In one embodiment, the amount of acid added in step c') is 0.3 to 40 mol %, preferably 0.4 to 15 mol %, more preferably 0.5 to 5 mol %, most preferably 0.6 to 3 mol %, based on the molar amount of the ethylenically unsaturated compound used in step a).

EXAMPLES

The examples which follow illustrate the invention.
General Procedures
All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

Phosphorus trichloride (Aldrich) was distilled under argon before use. All preparative operations were effected in baked-out vessels. The products were characterized by means of NMR spectroscopy. Chemical shifts (δ) are reported in ppm. The $^{31}$P NMR signals were referenced as follows: $SR_{31P}=SR_{1H}*(BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84).

The recording of nuclear resonance spectra was effected on Bruker Avance 300 or Bruker Avance 400, gas chromatography analysis on Agilent GC 7890A, elemental analysis on Leco TruSpec CHNS and Varian ICP-OES 715, and ESI-TOF mass spectrometry on Thermo Electron Finnigan MAT 95-XP and Agilent 6890 N/5973 instruments.

Preparation of Chloro-2-Pyridyl-Tert-Butylphosphine (Precursor A)

The Grignard for the synthesis of chloro-2-pyridyl-t-butylphosphine is prepared by the "Knochel method" with isopropylmagnesium chloride (Angew. Chem. 2004, 43, 2222-2226). The workup is effected according to the method of Budzelaar (Organometallics 1990, 9, 1222-1227).

Scheme 1: Synthesis of precursor A

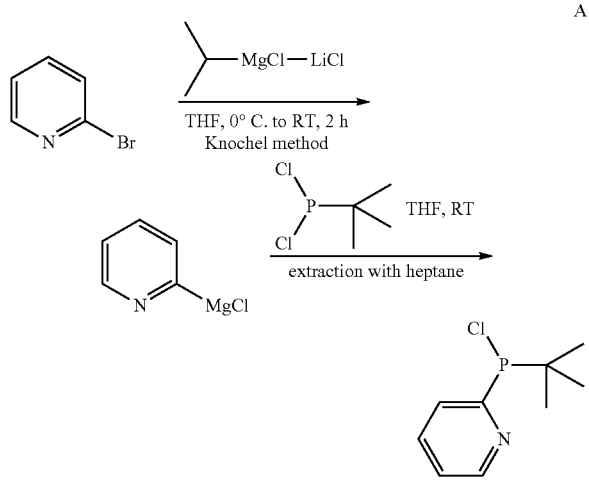

8.07 ml of a 1.3 M isopropylmagnesium chloride solution (Knochel's reagent) are introduced into a 50 ml round-bottom flask with magnetic stirrer and septum, and cooled to −15° C. Thereafter, 953.5 μl (10 mmol) of 2-bromopyridine are rapidly added dropwise. The solution immediately turns yellow. It is allowed to warm up to −10° C. The conversion of the reaction is determined as follows: about 100 μl solution are taken and introduced into 1 ml of a saturated ammonium chloride solution. If the solution "bubbles", not much Grignard has formed yet. The aqueous solution is extracted with a pipette of ether and the organic phase is dried over Na$_2$SO$_4$. A GC of the ethereal solution is recorded. When a large amount of pyridine has formed compared to 2-bromopyridine, conversions are high. At −10° C., there has been little conversion. After warming up to room temperature and stirring for 1-2 hours, the reaction solution turns brown-yellow. A GC test shows complete conversion. Now the Grignard solution can be slowly added dropwise with a syringe pump to a solution of 1.748 g (11 mmol) of dichloro-tert-butylphosphine in 10 ml of THF which has been cooled to −15° C. beforehand. It is important that the dichloro-tert-butylphosphine solution is cooled. At room temperature, considerable amounts of dipyridyl-tert-butylphosphine would be obtained. A clear yellow solution is initially formed, which then turns cloudy. The mixture is left to warm up to room temperature and to stir overnight. According to GC-MS, a large amount of product has formed. The solvent is removed under high vacuum and a whitish solid which is brown in places is obtained. The solid is suspended with 20 ml of heptane and the solid is comminuted in an ultrasound bath. After allowing the white solid to settle out, the solution is decanted. The operation is repeated twice with 10-20 ml each time of heptane. After concentration of the heptane solution under high vacuum, it is distilled under reduced pressure. At 4.6 mbar, oil bath 120° C. and distillation temperature 98° C., the product can be distilled. 1.08 g of a colourless oil are obtained. (50%).

Analytical data: $^1$H NMR (300 MHz, C$_6$D$_6$): δ 8.36 (m, 1H, Py), 7.67 (m, 1H, Py), 7.03-6.93 (m, 1H, Py), 6.55-6.46 (m, 1H, Py), 1.07 (d, J=13.3 Hz, 9H, t-Bu).

$^{13}$C NMR (75 MHz, C$_6$D$_6$): δ 162.9, 162.6, 148.8, 135.5, 125.8, 125.7, 122.8, 35.3, 34.8, 25.9 and 25.8.

$^{31}$P NMR (121 MHz, C$_6$D$_6$) δ 97.9.

MS (EI) m:z (relative intensity) 201 (M$^+$,2), 147(32), 145 (100), 109 (17), 78 (8), 57.1 (17).

Preparation of 1,1'-bis(tert-butyl-2-pyridylphosphino)ferrocene (compound 8)

Chemicals used:
6.4 g of ferrocene (34.4 mmol)
11 ml of TMEDA (8 g, 68.9 mmol, 2 eq)
44.1 ml of 1.6N butyllithium (hexane) (70.6 mmol, 2.05 eq)
12.5 ml (13.7 g, 68 mmol) of chloro(tert-butyl-2-pyridyl)phosphine
absolute heptane, absolute water, Na$_2$SO$_4$ (anhydrous)

In a 250 ml three-neck flask provided with a low-temperature thermometer, a magnetic stirrer and reflux condenser, 6.4 g of ferrocene are weighed out under argon and 70 ml of absolute heptane are added. The ferrocene dissolves completely. Thereafter, 11 ml of TMEDA are added to the solution, followed by 44.1 ml of 1.6 N n-BuLi. The reaction solution is left to stand at room temperature overnight. A solid forms (large orange crystals). The supernatant solution is removed. 100 ml of heptane are added to the solids, the mixture is cooled to about 5° C. by means of an ice bath and then 12.5 ml of chloro(tert-butyl-2-pyridyl)phosphine dissolved in 10 ml of heptane are slowly added dropwise within half an hour. The large crystals dissolve gradually and a precipitate of lithium chloride is formed. This suspension is stirred at 5° C. for half an hour and then at room temperature for one hour. The organic phase is washed three times with 20 mi each time of degassed water. Subsequently, the organic phase is dried over $Na_2SO_4$ (anhydrous), the sodium sulphate is filtered off, the sodium sulphate is washed three times with 20 ml each time of heptane and the combined solution is dried under reduced pressure. An orange oil forms, which crystallizes fully in the refrigerator overnight. Yield: 17.1 g=96%.

Analytical Data:

$^1$H NMR (300 MHz, $C_6D_6$): δ 8.66-8.56 (m, 2H, Py), 7.76-7.69 (m, 2H, Py), 7.08-6.97 (m, 2H, Py), 6.69-6.61 (m, 2H, Py), 5.17 (m, 1H, ferrocenyl), 4.94 (m, 1H, ferrocenyl), 4.37 (m, 1H, ferrocenyl), 4.17 (m, 1H, ferrocenyl), 4.05 (m, 1H, ferrocenyl), 3.98-3.93 (m, 3H, ferrocenyl), 1.14 (d, J=12.7 Hz, 9H, t-Bu), 1.12 (d, J=12.7 Hz, 9H, t-Bu).

$^{13}$C NMR (75 MHz, $C_6D_6$): δ 163.6, 163.5, 149.8, 149.8, 149.6, 134.6, 134.4, 132.5, 132.4, 132.0, 132.0, 122.7, 78.4, 78.0, 77.9, 77.6, 74.2, 74.1, 74.0, 74.0, 73.8, 72.6, 72.4, 71.7, 71.6, 71.5, 31.8, 31.7, 31.7, 31.6, 28.3 and 28.2.

$^{31}$P NMR (121 MHz, $C_6D_6$) δ 7.3 and 7.1

Separation of the Diastereomer Forms of Compound 8

As apparent from the two closely adjacent phosphine signals at δ 7.3 and 7.1 ppm, the compound 8 is in two diastereomer forms. These were separated from one another as follows.

First the respected borane adducts of the diastereomer mixture were prepared, and then they were separated by column chromatography. It was possible to isolate three products: the respective diastereomeric borane adducts and a monosubstituted by-product.

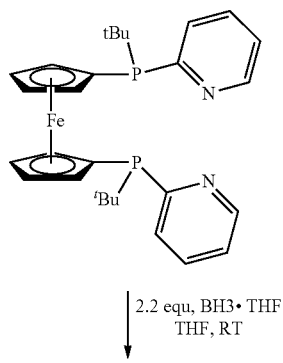

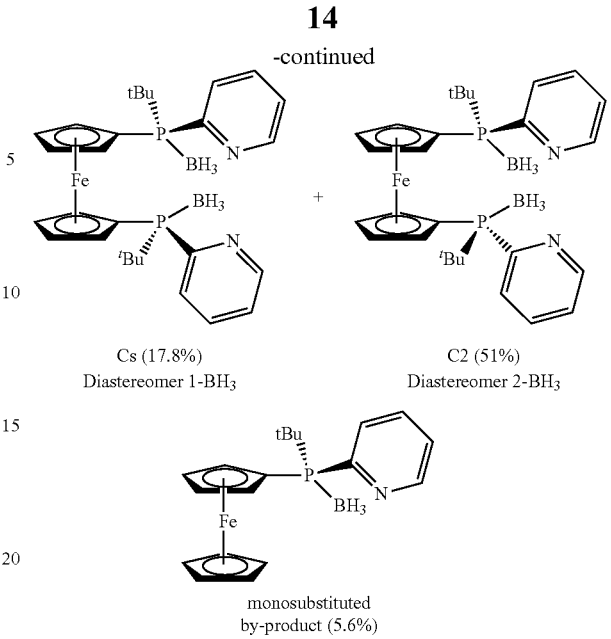

Cs (17.8%)
Diastereomer 1-BH$_3$

C2 (51%)
Diastereomer 2-BH$_3$ monosubstituted
by-product (5.6%)

Scheme 2: Synthesis of the borane adducts; Cs: mirror symmetry based on the plane through the Fe atom at right angles to the molecule axis; C2: twofold symmetry based on the rotation about the Fe atom A 50 ml round-bottom flask with nitrogen tap and magnetic stirrer bar is initially charged under argon with 700 mg (1.36 mmol) of the red-brown bis(2-pyridyl-tert-butylphosphino)ferrocene ligand and closed with a septum. After addition of 10 ml of THF, a clear orange-red solution has formed. At room temperature, 2.99 ml (2.2 eq, 2.99 mmol) of a 1 M borane solution are now added rapidly. After stirring for 2 days, there is still a clear orange-red solution. A thin-layer chromatogram clearly shows two products which can be stained with $KMnO_4$ solution. $R_{f1}$=0.15, $R_{f2}$=0.31 (ethyl acetate:heptane=1:7). The borane adduct is chromatographed twice with a Combiflash apparatus (CombiFlash® Rf, TELEDYNE ISCO, A Teledyne Technologies Company) (pure heptane for 5 min, then the ethylene content is increased to 5% within 40 min). In the first run, it is possible to isolate the quickly eluting monosubstituted borane adduct. Yield: 28 mg (5.6%). In the second run, the diastereomer 1-BH$_3$ is obtained in a 132 mg (17.9%) yield, and the somewhat more slowly eluting diastereomer 2-BH$_3$ in a 376 mg (51%) yield. Both compounds are orange-brown solids.

Monosubstituted by-product: $^1$H NMR (300 MHz, CDCl$_3$): δ 8.87 (m, 1H, py), 8.30 (m, 1H, py), 7.83 (m, 1H, py), 7.43 (m, 1H, py), 5.21 (m, 1H, ferrocenyl), 4.74 (m, 1H, ferrocenyl), 4.43 (m, 1H, ferrocenyl), 3.82 (s, 5H, Cp$^-$), 1.01 (d, J=14.5 Hz, 9H, tBu), 1.60-0.36 (br, BH$_3$).

$^{13}$C NMR (75 MHz, CDCl$_3$): δ 149.4, 149.3, 135.7, 135.5, 130.5, 130.2 (Py), 75.8, 75.6, 74.1, 71.9, 71.8, 70.6, 70.4 (ferrocenyl), 69.5 (Cp$^-$), 31.5, 31.1 and 25.9 (tBu).

$^{31}$P NMR (121 MHz, $C_6D_6$) δ 30.3 (m(br), P—BHS), yield: yellow oil, 28 mg (5.6%).

Diastereomer 1-BH$_3$ (Cs): $^1$H NMR (300 MHz, CDCl$_3$): δ 8.91 (m, 2H, py), 8.26 (m, 2H, py), 7.83 (m, 2H, py), 7.44 (m, 2H, py), 5.25 (m, 2H, ferrocenyl), 4.24 (m, 2H, ferrocenyl), 4.07 (m, 2H, ferrocenyl), 3.62 (m, 2H, ferrocenyl), 0.99 (d, J=14.0 Hz, 18H, tBu), 1.54-0.19 (br, BH$_3$, poorly resolved)).

$^{13}$C NMR (75 MHz, CDCl$_3$): δ 154.7, 153.7, 149.7, 149.6, 135.6, 135.4, 130.3, 130.0, 124.8, 124.7 (Py), 76.1, 75.6, 75.9, 75.2, 74.7, 74.6, 72.9, 72.7, 66.3 and 65.5 (ferrocenyl), 31.4, 30.9, 25.8 and 25.7 (tBu)

$^{31}$P NMR (121 MHz, C$_6$D$_6$) δ 29.9 (d (br), J=68.1 Hz, P—BH$_3$), yield: 132 mg (17.9%), orange solid.

Diastereomer 2-BH$_3$ (C2): $^1$H NMR (300 MHz, CDCl$_3$): δ 8.88 (m, 2H, py), 8.28 (m, 2H, py), 7.85 (m, 2H, py), 7.47 (m, 2H, py), 4.73 (m, 2H, ferrocenyl), 4.67 (m, 2H, ferrocenyl), 4.29 (m, 2H, ferrocenyl), 3.57 (m, 2H, ferrocenyl), 0.98 (d, J=14.6 Hz, 18H, tBu), 1.61-0.25 (br, BH$_3$, poorly resolved)).

$^{13}$C NMR (75 MHz, CDCl$_3$): δ 154.8, 153.9, 149.3, 149.2, 135.7, 135.6, 130.5, 130.2, 124.8 (Py), 76.3, 74.8, 74.7, 74.6, 73.2, 73.1, 66.1 and 65.3 (ferrocenyl), 31.4, 31.0 and 25.8 (tBu).

$^{31}$P NMR (121 MHz, C$_6$D$_6$) δ 30.1 (d (br), J=63.7 Hz, P—BH$_3$). Yield: 376 mg (51%), orange solid.

The free phosphine ligands (diastereomer 1 (Cs) 8.1 and diastereomer 2 (C2) 8.2) can be prepared from the borane adducts by the following method:

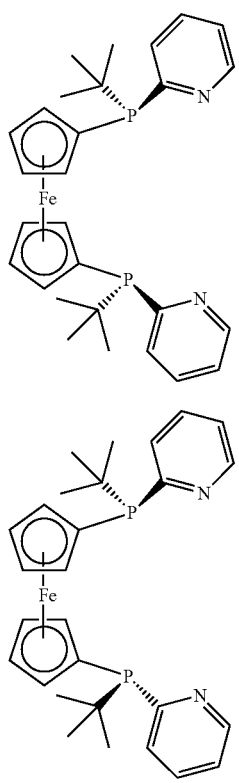

8.1 (Cs)

8.2 (C2)

In a 50 ml round bottom flask with magnetic stirrer bar which has been inertized by evacuating and filling within inert gas, 376 mg of diastereomer-2-BH$_3$ (C2) are weighed out under argon and the flask is closed with a septum. Then 7 ml of absolute morpholine are added and an orange suspension forms, which gradually dissolves at 50° C. on a water bath to give a clear orange solution. According to the thin-layer chromatogram and $^{31}$P NMR, the borane adduct has been fully converted to the free phosphine after 4 hours. After the now clear orange solution has cooled down, the morpholine is removed in an oil pump vacuum and the orange residue is chromatographed. The chromatography is necessary in order to separate the product from the morpholine-borane adduct. First of all, the eluent 2:1 (heptane/ethyl acetate) is freed of dissolved oxygen by passing argon gas through it for one hour. A 250 ml three-neck flask with septum, nitrogen connection and a column filled with silica gel 60 is sealed at the top with a further septum, inertized by repeated evacuation and filling with argon and eluted with the eluent. The orange residue is dissolved in 2-3 ml of eluent and applied to the column. The phosphine can now be chromatographed by applying eluent to the column under argon via a transfer needle. It is easy to see the end of the chromatography by the orange colour of the product. The chromatographed orange solution is transferred into a nitrogen flask with a syringe and freed of the solvent under high vacuum. A viscous yellow oil is obtained, which gradually solidifies. Yield 312 mg (87.3%)

Diastereomer 2 (C2) 8.2: $^1$H NMR (300 MHz, C$_6$D$_6$): δ 8.58 (m, 2H, py), 7.72 (t,t, J=7.8 Hz, 1.3 Hz, 2H, py), 7.02 (t,t, J=7.6 Hz, J=2.1 Hz, 2H, py), 6.68-6.62 (m, 2H, py), 4.93 (m, 2H, ferrocenyl), 4.37 (m, 2H, ferrocenyl), 3.95 (m, 4H, ferrocenyl), 1.13 (d, J=12.0 Hz, 18H, tBu).

$^{13}$C NMR (75 MHz, CDCl$_3$): δ 163.6 and 163.4 (C), 149.6, 149.5, 134.6, 134.4, 132.6, 131.9, 122.7 (py), 78.5, 77.9, 74.0, 73.9, 73.7, 72.5, 71.7, 71.5 (ferrocenyl), 31.8 31.6, 28.3 and 28.1 (tBu).

$^{31}$P NMR (121 MHz, C$_6$D$_6$) δ 7.1.

HRMS (ESI) m/z$^+$ calculated for C$_2$eHFeN$_2$P$_2$(M+H)$^+$ 517.16197; found: 517.16221.

In an analogous manner, it is also possible to prepare the other diastereomer-1 (Cs) 8.1. Here, 318 mg of the borane adduct are used and, after chromatography, 219 mg (73%) of the red-orange diastereomer-1 (Cs) 8.1 are obtained.

Diastereomer 1 (Cs) 8.1: $^1$H NMR (300 MHz, C$_6$D$_6$): δ 8.63 (m, 2H, py), 7.72 (t,t, J=7.8 Hz, 1.1 Hz, 2H, py), 7.04 (t,t, J=7.6 Hz, J=2.1 Hz, 2H, py), 6.66 (m, 2H, py), 5.17 (m, 2H, ferrocenyl), 4.17 (m, 2H, ferrocenyl), 4.05 (m, 2H, ferrocenyl), 3.95 (m, 2H, ferrocenyl), 1.11 (d, J=12.3 Hz, 18H, tBu).

$^{13}$C NMR (75 MHz, C$_6$D$_6$): δ 163.5 and 163.3 (C), 149.7, 149.6, 134.5, 134.3, 132.4, 131.8 and 122.6 (py), 77.9, 77.4, 74.1, 74.0, 73.8, 72.3, 71.5 and 71.4 (ferrocenyl), 31.7, 31.5, 28.2 and 28.0 (tBu).

$^{31}$P NMR (121 MHz, C$_6$D$_6$) δ 7.2.

HRMS (ESI) m/z$^+$ calculated for CaH$_3$FeN$_2$P$_2$(M+H)$^+$ 517.16197; found 517.16221.

An isomer ratio 8.2:8.1 (C2:Cs) of 56:43 (NMR spectra) can be determined from the diastereomer mixture.

Preparation of the Palladium Complexes K5.1 and K5.2

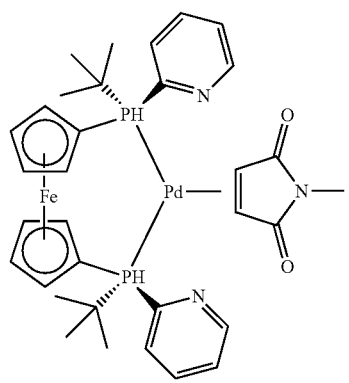

K5.1a and K5.1b

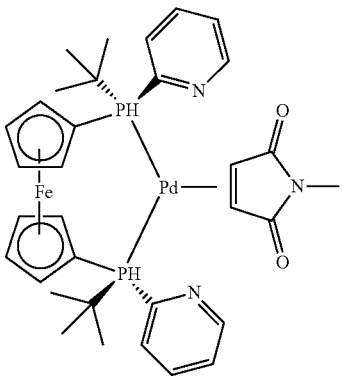

K5.2

The corresponding palladium complexes K5.1a and K5.1b with Cs symmetry and the complex K5.2 with C1 symmetry are prepared from the diastereomeric pure phosphine ligands 8.1 and 8.2 in the presence of maleimide in heptane as follows:

Complex K5.2: 58.1 mg (0.274 mmol) of palladium precursor (cyclopentadienyl allyl palladium) are weighed out in a 10 ml Schlenk vessel and dissolved in 5 ml of freeze-thawed heptane. The red clear solution is filtered through Celite into a nitrogen-inertized 25 ml flask. In a second Schlenk vessel under argon, 150 mg (0.29 mmol) of diastereomer 8.2 (C2) and 30.4 mg (0.274 mmol) of N-methylmaleimide are dissolved in 6 ml of heptane. The N-methylmaleimide only goes completely into solution by heating at 60° C. on a water bath. The clear yellow-orange solution is slowly added dropwise at room temperature to the red palladium precursor solution with a syringe pump. The solution lightens in colour and a yellow precipitate forms. The next day, the precipitate is left to settle out and the supernatant solution is decanted. After washing three times with 1-2 ml of heptane, the yellow precipitate is dried by suction on an oil pump. 200 mg (95%) of a yellow solid are obtained. According to $^{31}$P NMR a C1-symmetric complex must have formed from the C2-symmetric ligand, as shown by the characteristic two doublets.

$^{1}$H NMR (300 MHz, C$_6$D$_6$): δ 8.48 (m, 2H, py), 8.12 (m, 2H, py), 7.13 (m, 1H, py), 7.02 (t,t, J=7.6 Hz, J=2.3 Hz, 1H, py), 6.63 (m, 2H, py), 5.32 (m, 1H, ferrocenyl), 4.89 (m, 1H, ferrocenyl), 4.45 (m, 2H, ferrocenyl), 3.95 (m, 1H, ferrocenyl), 3.92 (m, 2H, ferrocenyl), 3.85 (m; 2H, ferrocenyl), 3.44 (m; 1H, ferrocenyl), 3.03 (s, 3H, NMe), 1.36 (d, J=14.9 Hz, 9H, tBu), 1.32 (d, J=14.6 Hz, 9H, tBu).

$^{13}$C NMR (75 MHz, C$_6$D$_6$): δ 175.9 and 175.8 (CO), 160.2, 159.7, 158.5 and 158 (C), 149.5, 149.4, 135.6, 135.4, 135.1, 135.0, 134.8, 134.5, 133.9, 124.3, 123.9 (py), 78.6, 78.3, 76.8, 76.5, 75.0, 74.8, 74.4, 74.2, 73.8, 73.4, 72.7, 72.6, 72.5, 71.0, 70.5, 70.4 (ferrocenyl), 52.6, 52.5, 52.2, 52.1, 51.1, 51.0, 50.7, 50.6 (maleimide), 35.5 35.3, 35.1, 28.1, 28.0, 27.4, 27.3 (tBu), 23.5 (NMe).

$^{31}$P NMR (121 MHz, C$_6$D$_6$) δ 47.3 (d, J=16 Hz), 46.4 (d, J=16 Hz).

Complex K5.1: The preparation of K5.1 from the diastereomer 8.1 is effected analogously to the preparation of K5.2.

$^{1}$H NMR (300 MHz, C$_6$D$_6$): δ 8.27 (m, 2.77H, py), 7.74 (t, J=7.3 Hz, 2H, py), 7.62 (m, 0.77H, py), 6.81 (t,t, J=7.7 Hz, J=2.2 Hz, 2H, py), 6.66 (t,t, J=7.7 Hz, J=2.1 Hz, 0.77H, py), 6.39 (m, 2.77H, py), 4.66 (m, 0.77H, methine), 4.49 (m, 2H, methine), 4.42 (m, 0.77H, methine), 4.33 (m, 2H, methine), 4.27 (m; 2H, methine I), 4.19 (m; 0.77H, methine), 4.05 (m; 2.77H, methine), 3.95 (m; 2.77H, methine), 3.10 (s, 3H, NMe), 3.03 (s, 1.21H, NMe), 1.36 (d, J=13.9 Hz, 25.26H, tBu).

$^{31}$P NMR (121 MHz, C$_6$D$_6$) δ 46.9 and 46.3. Yield: 46 mg, (90%), yellow solid.

It is apparent from the $^{1}$H NMR spectra that the ligand 8.1 (Cs) reacts to give two diastereomeric Cs-symmetric palladium complexes K5.1a and K5.1b (Cs) in a ratio of 72:28, since the maleimide can assume two distinguishable positions. The ratio can be determined from the area integrals of the N-methyl groups at 3.10 and 3.03 ppm in the $^{1}$H NMR. The $^{31}$P NMR likewise shows two singlets, which can be assigned to the two possible diastereomeric complexes having Cs symmetry.

The ligand diastereomer 8.2 (C2), by contrast, leads to a homogeneous complex with C1 symmetry. As a result of the firm binding of maleimide to the metal centre, the C2 symmetry is lost, but a rotation of the maleimide by 180°, by contrast with the diastereomer 8.1 (Cs), would not lead to a new isomer. Here, the maleimide shows just one singlet at 3.03 ppm in the $^{1}$H NMR and, owing to the C1 symmetry, 2 doublets in the $^{31}$P NMR.

General Method for Performance of the High-Pressure Experiments

General Experimental Method for Autoclave Experiments in Glass Vials:

A 300 ml Parr reactor is used. Matched to this is an aluminium block of corresponding dimensions which has been manufactured in-house and which is suitable for heating by means of a conventional magnetic stirrer, for example from Heidolph. For the inside of the autoclave, a round metal plate of thickness about 1.5 cm was manufactured, containing 6 holes corresponding to the external diameter of the glass vials. Matching these glass vials, they are equipped with small magnetic stirrers. These glass vials are provided with screw caps and suitable septa and charged, using a special apparatus manufactured by glass blowers, under argon with the appropriate reactants, solvents and catalysts and additives. For this purpose, 6 vessels are filled at the same time; this enables the performance of 6 reactions at the same temperature and the same pressure in one experiment. Then these glass vessels are closed with screw caps and septa, and a small syringe cannula of suitable size is used to puncture each of the septa. This enables gas exchange later in the reaction. These vials are then placed in the metal plate and these are transferred into the autoclave under argon. The autoclave is purged with CO and filled at room temperature with the CO pressure intended. Then, by means of the magnetic stirrer, under magnetic stirring, the autoclave is heated to reaction temperature and the reaction is conducted for the appropriate period. Subsequently, the autoclave is cooled down to room temperature and the pressure is slowly released. Subsequently, the autoclave is purged with nitrogen. The vials are taken from the autoclave, and a defined amount of a suitable standard is added. A GC analysis is effected, the results of which are used to determine yields and selectivities.

Analysis

GC analysis: for the GC analysis, an Agilent 7890A gas chromatograph having a 30 m HP5 column is used. Temperature profile: 35° C., 10 min; 10° C./min to 200° C.; the injection volume is 1 μl with a split of 50:1.

Retention time for iso-C9 esters 19.502-20.439 min (main peak: 19.990 min)

Retention time for n-C9 esters: 20.669, 20.730, 20.884, 21.266 min.

Evaluation of the Experiments

The n selectivities reported hereinafter relate to the proportion of terminal methoxycarbonylation based on the overall yield of methoxycarbonylation products.

Methoxycarbonylation of 1-octane

In order to examine the activity of the diastereomers K5.1 and K5.2 of the complex [Pd(Cp$_2$Fe)(P(2-pyridyl)(t-butyl))$_2$ η$^2$-(N-methylmaleimide)], a mixture of K5.1 and K5.2 is used in a molar ratio of 40:60.

The benchmark reaction used is the methoxycarbonylation of 1-octene to methyl nonanoate.

Scheme 3: Reaction of 1-octene with methanol; the linear reaction product is shown.

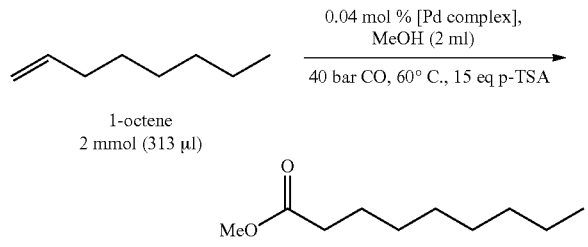

In the experiments, the reaction conditions are chosen such that complete conversion cannot take place (40 bar CO, 60° C., T=variable). In order to conduct the experiments, 2 stock solutions are prepared. One stock solution consists of the complex mixture (2.93 mg [Pd] in 5 ml of MeOH); the other stock solution consists of the acid (22.8 mg para-toluenesulphonic acid in 10 ml of MeOH). One milliliter in each case of stock solution are added to a 4 ml vial equipped with septum, cannula and a small magnetic stirrer bar under argon and and the vial is placed in a carousel, which is placed in turn into a 300 ml Parr autoclave. After purging with argon and CO, CO is injected to 40 bar and the autoclave is then placed into an aluminium block preheated to 60° C.

Three experiments of this kind are conducted with variation in the reaction times of 15 minutes, 30 minutes and 40 minutes. After the reaction, the autoclave is brought to room temperature and cautiously decompressed. Then 300 µl of isooctane are added as standard for the quantitative GC determination and mixed well. The results are compiled in the following table:

| Catalyst | Ester yield (%) | n selectivity (%) | Reaction time (min) |
|---|---|---|---|
| Mixture of K5.2 and K5.1 | 15 | 83 | 15 |
| Mixture of K5.2 and K5.1 | 53 | 82 | 30 |
| Mixture of K5.2 and K5.1 | 65 | 82 | 40 |

It is apparent from Table 3 that the diastereomer mixture according to the invention has very good catalytic properties for the alkoxycarbonylation of ethylenically unsaturated compounds, especially of long-chain olefins. It is thus possible to dispense with a diastereomer separation.

The invention claimed is:
1. Diastereomer mixture comprising diastereomers of the formulae (I.1) and (I.2)

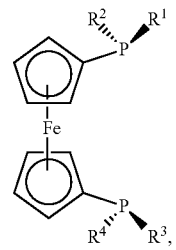
(I.1)

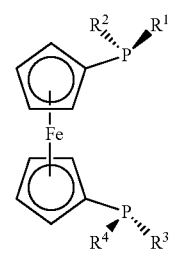
(I.2)

where
R$^2$, R$^4$ are each independently selected from —(C$_1$-C$_{12}$)-alkyl, —(C$_3$-C$_{12}$)-cycloalkyl, —(C$_3$-C$_{12}$)-heterocycloalkyl, —(C$_3$-C$_{20}$)-aryl;

the R$^1$, R$^3$ radicals are each a —(C$_3$-C$_{20}$)-heteroaryl radical;

R$^1$, R$^3$ may each independently be substituted by one or more substituents selected from —(C$_1$-C$_{12}$)-alkyl, —(C$_3$-C$_{12}$)-cycloalkyl, —(C$_3$-C$_{12}$)-heterocycloalkyl, —O—(C$_1$-C$_{12}$)-alkyl, —O—(C$_1$-C$_{12}$)-alkyl-(C$_6$-C$_{20}$)-aryl, —O—(C$_3$-C$_{12}$)-cycloalkyl, —S—(C$_1$-C$_{12}$)-alkyl, —S—(C$_3$-C$_{12}$)-cycloalkyl, —COO—(C$_1$-C$_{12}$)-alkyl, —COO—(C$_3$-C$_{12}$)-cycloalkyl, —CONH—(C$_1$-C$_{12}$)-alkyl, —CONH—(C$_3$-C$_{12}$)-cycloalkyl, —CO—(C$_1$-C$_{12}$)-alkyl, —CO—(C$_3$-C$_{12}$)-cycloalkyl, —N—[(C$_1$-C$_{12}$)-alkyl]$_2$, —(C$_6$-C$_{20}$)-aryl, —(C$_6$-C$_{20}$)-aryl-(C$_1$-C$_{12}$)-alkyl, —(C$_6$-C$_{20}$)-aryl-O—(C$_1$-C$_{12}$)-alkyl, —(C$_3$-C$_{20}$)-heteroaryl, —(C$_3$-C$_{20}$)-heteroaryl-(C$_1$-C$_{12}$)-alkyl, —(C$_3$-C$_{20}$)-heteroaryl-O—(C$_1$-C$_{12}$)-alkyl, —COOH, —OH, —SO$_3$H, —NH$_2$, halogen;

and
R$^2$, R$^4$, if they are —(C$_1$-C$_{12}$)-alkyl, —(C$_3$-C$_{12}$)-cycloalkyl, —(C$_3$-C$_{12}$)-heterocycloalkyl or —(C$_6$-C$_{20}$)-aryl, may each independently be substituted by one or more substituents selected from —(C$_1$-C$_{12}$)-alkyl, —(C$_3$-C$_{12}$)-cycloalkyl, —(C$_3$-C$_{12}$)-heterocycloalkyl, —O—(C$_1$-C$_{12}$)-alkyl, —O—(C$_1$-C$_{12}$)-alkyl-(C$_6$-C$_{20}$)-aryl, —O—(C$_3$-C$_{12}$)-cycloalkyl, —S—(C$_1$-C$_{12}$)-alkyl, —S—(C$_3$-C$_{12}$)-cycloalkyl, —COO—(C$_1$-C$_{12}$)-alkyl, —COO—(C$_3$-C$_{12}$)-cycloalkyl, —CONH—(C$_1$-C$_{12}$)-alkyl, —CONH—(C$_3$-C$_{12}$)-cycloalkyl, —CO—(C$_1$-C$_{12}$)-alkyl, —CO—(C$_3$-C$_{12}$)-cycloalkyl, —N—[(C$_1$-C$_{12}$)-alkyl]$_2$, —(C$_6$-C$_{20}$)-aryl, —(C$_6$-C$_{20}$)-aryl-(C$_1$-C$_{12}$)-alkyl, —(C$_6$-C$_{20}$)-aryl-O—(C$_1$-C$_{12}$)-alkyl, (C$_3$-C$_{20}$)-heteroaryl, —(C$_3$-C$_{20}$)-heteroaryl-(C$_1$-C$_{12}$)-alkyl, —(C$_3$-C$_{20}$)-heteroaryl-O—(C$_1$-C$_{12}$)-alkyl, —COOH, —OH, —SO$_3$H, —NH$_2$, halogen.

2. Diastereomer mixture according to claim 1, where the molar ratio of (I.1) to (I.2) is in the range from 10:90 to 70:30.

3. Diastereomer mixture according to claim 1, where R$^2$, R$^4$ are each independently selected from —(C$_1$-C$_{12}$)-alkyl, cyclohexyl and phenyl.

4. Diastereomer mixture according to claim 1, where $R^1$, $R^3$ are each a heteroaryl radical having five to ten ring atoms.

5. Diastereomer mixture according to claim 1, where $R^1$, $R^3$ are each pyridyl.

6. Diastereomer mixture according to claim 1, where $R^1$, $R^3$ are each identical radicals and $R^2$, $R^4$ are each identical radicals.

7. Diastereomer mixture according to claim 1, where the diastereomers I.1 and I.2 are compounds of the formula (8.1) and (8.2)

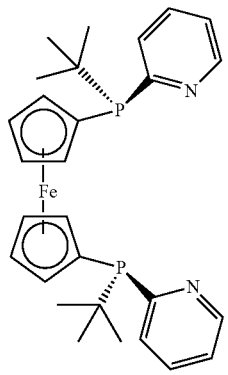

(8.1)

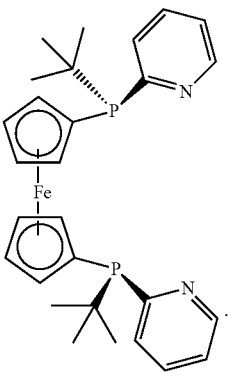

(8.2)

8. Complex mixture comprising a first complex comprising Pd and a diastereomer of formula (I.1) and a second complex comprising Pd and a diastereomer of formula (I.2); each formula according to claim 1.

9. Process comprising the following process steps:
a) Initially charging an ethylenically unsaturated compound;
b) adding a diastereomer mixture according to claim 1 and a compound comprising Pd;
c) adding an alcohol;
d) feeding in CO;
e) heating the reaction mixture, with conversion of the ethylenically unsaturated compound to an ester.

10. Process according to claim 9,
wherein the ethylenically unsaturated compound comprises 2 to 30 carbon atoms and optionally one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, hydroxyl, sulphhydryl, amino, ether, thioether, aryl, heteroaryl or silyl groups and/or halogen substituents.

11. Process according to claim 9,
wherein the ethylenically unsaturated compound is selected from ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, and mixtures thereof.

12. Process according to claim 9,
wherein the ethylenically unsaturated compound comprises 6 to 22 carbon atoms.

13. Process according to claim 9,
wherein the compound comprising Pd in process step b) is selected from palladium dichloride, palladium(II) acetylacetonate, palladium(II) acetate, dichloro(1,5-cyclooctadiene)palladium(II), bis(dibenzylideneacetone)palladium, bis(acetonitrile)dichloropalladium(II), palladium(cinnamyl) dichloride.

14. Process according to claim 9,
wherein the alcohol in process step c) is selected from methanol, ethanol, 1-propanol, 1-butanol, 1-pentanol, 1-hexanol, 2-propanol, tert-butanol, 3-pentanol, cyclohexanol, phenol, and mixtures thereof.

15. A process for the catalysis of an alkoxycarbonylation reaction, comprising introducing the compound according to claim 1.

16. Process comprising the following process steps:
a) initially charging an ethylenically unsaturated compound;
b) adding a complex mixture according to claim 8;
c) adding an alcohol;
d) feeding in CO;
e) heating the reaction mixture, with conversion of the ethylenically unsaturated compound to an ester.

17. Process according to claim 16,
wherein the ethylenically unsaturated compound comprises 2 to 30 carbon atoms and optionally one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, hydroxyl, sulphhydryl, amino, ether, thioether, aryl, heteroaryl or silyl groups and/or halogen substituents.

18. Process according to claim 16,
wherein the ethylenically unsaturated compound is selected from ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, and mixtures thereof.

19. Process according to claim 16,
wherein the alcohol in process step c) is selected from methanol, ethanol, 1-propanol, 1-butanol, 1-pentanol, 1-hexanol, 2-propanol, tert-butanol, 3-pentanol, cyclohexanol, phenol, and mixtures thereof.

20. A process for the catalysis of an alkoxycarbonylation reaction comprising; introducing the complex mixture according to claim 8.

* * * * *